United States Patent [19]

Kikumoto et al.

[11] Patent Number: 4,684,651

[45] Date of Patent: Aug. 4, 1987

[54] ALKYLENEDIOXYBENZENE AND ACID ADDITION SALTS THEREOF USEFUL AS HYPOTENSIVES

[75] Inventors: Ryoji Kikumoto, Machida; Harukazu Fukami, Yokohama; Kenichiro Nakao; Mamoru Sugano, both of Tokyo, all of Japan

[73] Assignee: Mitsubishi Chemical Industries Limited, Tokyo, Japan

[21] Appl. No.: 352,716

[22] Filed: Feb. 26, 1982

[30] Foreign Application Priority Data

Mar. 17, 1981 [JP] Japan .................................. 56-38233
Mar. 17, 1981 [JP] Japan .................................. 56-38234

[51] Int. Cl.$^4$ .................. A61K 31/495; C07D 405/06; C07D 405/12; C07D 405/14
[52] U.S. Cl. .................................... 514/253; 544/360; 544/377
[58] Field of Search ................. 544/360, 377; 514/253

[56] References Cited

U.S. PATENT DOCUMENTS 3,562,277  2/1971  Hansen et al. ...................... 544/377
3,729,474  4/1973  Mentrup et al. .................... 544/377
3,928,358  12/1975  Renth et al. ....................... 544/377
4,100,282  7/1978  Renth et al. ....................... 544/377

FOREIGN PATENT DOCUMENTS 103893  8/1979  Japan .................................. 544/377
7210147  1/1973  Netherlands ....................... 514/253

Primary Examiner—Nicholas S. Rizzo
Assistant Examiner—Cecilia Shen
Attorney, Agent, or Firm—Oblon, Fisher, Spivak, McClelland & Maier

[57] ABSTRACT

Alkylenedioxybenzene derivatives are prepared and found to be useful as pharmaceutical agents, particularly as hypotensives.

3 Claims, No Drawings

ALKYLENEDIOXYBENZENE AND ACID ADDITION SALTS THEREOF USEFUL AS HYPOTENSIVES

BACKGROUND OF THE INVENTION

Field of the Invention

This invention relates to alkylenedioxybenzene derivatives and acid addition salts thereof having hypotensive activities.

SUMMARY OF THE INVENTION

The compounds according to this invention are represented by the formula:

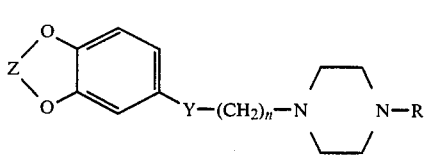

wherein n is an integer of 1 to 6; Z is —$(CH_2)_m$— where m is an integer of 1 to 3 or

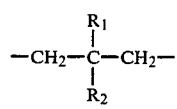

where $R_1$ is hydrogen or $C_1$-$C_3$ alkyl and $R_2$ is $C_1$-$C_3$ alkyl; Y is —CH(OH)—,

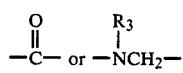

where $R_3$ is hydrogen, $C_1$-$C_3$ alkyl or $C_1$-$C_3$ acyl; and R is phenyl which may optionally have one or more substituents selected from halogen, $C_1$-$C_5$ alkyl, $C_1$-$C_5$ alkoxy and trifluoromethyl, or pyridyl.

Also encompassed within this invention are acid addition salts thereof.

The compounds of this invention can be used effectively as hypotensives.

DESCRIPTION OF THE PREFERRED EMBODIMENTS

As summarized above, this invention relates to a group of the compounds useful as hypotensives, the structure is as follows:

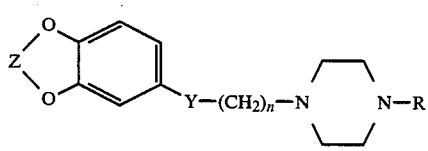

wherein n is an integer of 1 to 6; Z is —$(CH_2)_m$— where m is an integer of 1 to 3 or

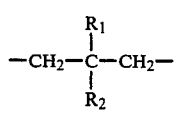

where $R_1$ is hydrogen or $C_1$-$C_3$ alkyl and $R_2$ is $C_1$-$C_3$ alkyl; Y is —CH(OH)—,

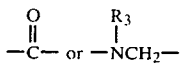

where $R_3$ is hydrogen, $C_1$-$C_3$ alkyl or $C_1$-$C_3$ acyl; and R is phenyl which may optionally have one or more substituents selected from halogen, $C_1$-$C_5$ alkyl, $C_1$-$C_5$ alkoxy and trifluoromethyl, or pyridyl.

The compounds according to this invention may be prepared by the following processes:

The compounds of Formula (I) wherein Y is

may be prepared by reacting an ω-haloalkanoylalkylenedioxybenzene compound of the formula:

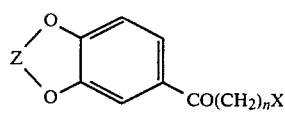

wherein n and Z are as defined in Formula (I) and X is a halogen atom, with a piperazine compound of the formula:

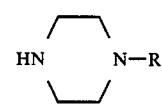

wherein R is as defined in Formula (I).

The compounds of Formula (I) wherein Y is —CH(OH)— may be prepared either by reducing the carbonyl group of an ω-piperazinylalkanoylalkylenedioxybenzene of the.formula:

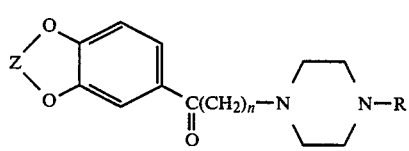

wherein n, Z and R are as defined in Formula (I), which is the product of the above reaction of compounds (II) and (III), or by reacting a compound of the formula:

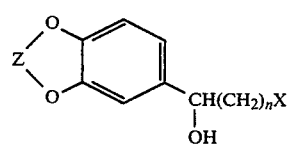

wherein n and Z are as defined in Formula (I) and X is a halogen atom, which is obtained by reduction of an ω-haloalkanoylalkylenedioxybenzene (II), with a piperazine compound (III). The compounds of Formula (I) wherein Y is —$NHCH_2$— may be prepared by reacting an ω-haloalkanoylalkylenedioxyaniline compound of the formula:

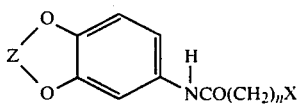

(VI)

wherein n and Z are as defined in Formula (I) and X is a halogen atom, with a piperazine compound (III) and then reducing the carbonyl group of the resultant ω-piperazinylalkanoylalkylenedioxyaniline of the formula:

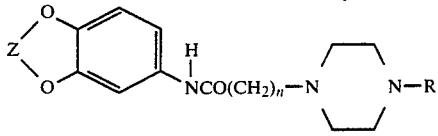

(VII)

wherein n, Z and R are as defined in Formula (I). The —NH— group of the thus obtained reaction product may be alkylated or acylated to give the corresponding aniline derivative.

These processes for preparing the compounds of this invention will be described below more fully. The ω-haloalkanoylalkylenedioxybenzene (II) or ω-haloalkanoylalkylenedioxyaniline (VI) and the piperazine usually react at a molar ratio of 1:1. However, the piperazine is preferably used in excess, since under such conditions the reaction usually proceeds more smoothly. Thus, the piperazine may be used in an amount of 1 to 10 moles per mole of the ω-haloalkanoylalkylenedioxybenzene or ω-haloalkanoylalkylenedioxyaniline.

While the reaction proceeds well even in the absence of solvents, an inert solvent may be used to allow the reaction to proceed more smoothly. Useful solvents include water, dioxane, tetrahydrofuran, dimethylformamide, dimethylsulfoxide, lower alcohols and a mixture of two or more of these solvents.

The reaction temperature is not critical and it is usually from room temperature to 150° C.

The reaction time depends on the reaction temperature, the reactivities of the starting materials and the particular solvent, if it is used, and it is usually within the range of 10 minutes to 50 hours.

A base may be added to bind the hydrogen halide formed by the reaction, thereby accelerating the reaction. The base useful for this purpose includes inorganic basic materials such as potassium hydroxide, potassium carbonate, sodium hydroxide, sodium hydrogen carbonate, sodium carbonate, etc., as well as organic tertiary amines such as pyridine, triethylamine, etc. The base is usually used in an amount of 1 to 5 moles per mole of the piperazine.

An acid addition salt of the compound (I) may be prepared from the reaction mixture by removing therefrom the excess amine(s) and the solvent, if present, by distillation or washing with water, and, if necessary, adding an aqueous solution of a strong base such as sodium hydroxide or potassium hydroxide to give the free ω-piperazinylalkanoylalkylenedioxybenzene or ω-piperazinylalkanoylalkylenedioxyaniline, which is then extracted into a suitable organic solvent such as ethyl acetate, ether, chloroform, benzene, toluene or the like.

The separated organic layer is neutralized by addition of the appropriate acid to give the desired acid addition salt.

The resulting ω-piperazinylalkanoylalkylenedioxybenzene (IV) or its acid addition salt may be dissolved in a lower alcohol or an etheric solvent such as diethyl ether or tetrahydrofuran and then reacted with a borohydride salt to produce an ω-piperazinyl-α-hydroxyalkylalkylenedioxybenzene of the formula:

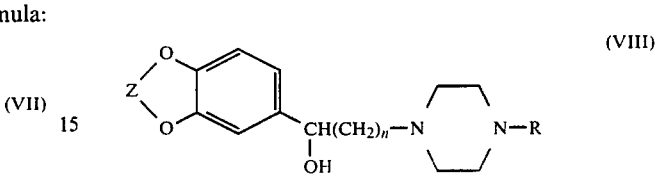

(VIII)

wherein n, Z and R are as defined in Formula (I).

In the cases where an acid addition salt is used, the solution is reacted with the borohydride as it is or after the acid addition salt therein has been converted to the free ω-piperazinylalkanoylalkylenedioxybenzene. After completion of the reaction, the reaction mixture is extracted with a suitable solvent such as ethyl acetate, ether, chloroform or benzene as it is or after it has been concentrated. The desired compound (VIII) is recovered from the extract in the form of a free base or the extract may be neutralized with an appropriate acid to give an acid addition salt.

A compound of the formula:

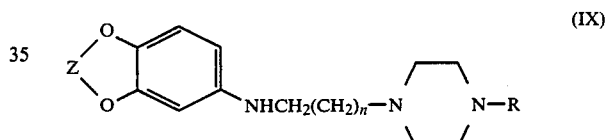

(IX)

wherein n, Z and R are as defined in Formula (I) may be prepared by dissolving the resulting ω-piperazinylalkanoylalkylenedioxyaniline (VII) or its acid addition salt in an etheric solvent such as ether or tetrahydrofuran, then, in the case of an acid addition salt, converting to the free ω-piperazinylalkanoylalkylenedioxyaniline, and treating the solution with lithium aluminum hydride. After completion of the reaction, the reaction mixture is worked up in a conventional manner, for example, by removing the aluminum hydroxide and lithium hydroxide by-products by filtration, then, if necessary, concentrating the filtrate, and extracting with ethyl acetate, ether, chloroform, benzene or the like. The desired compound (IX) may be recovered from the extract in the form of a free amine. If desired, the extract may be neutralized with an appropriate acid to give an acid addition salt. The resulting aniline derivative (IX) may be reacted with an alkyl halide, acyl halide or alkanoic acid anhydride in the presence of an inorganic basic material such as potassium carbonate or an organic base such as triethylamine or pyridine to give the corresponding alkylated or acylated aniline derivative.

Those ω-haloalkanoylalkylenedioxybenzene starting compounds of Formula (II) wherein n is an integer of 2 to 6 may be prepared by the Friedel-Crafts reaction of an ω-haloalkanoyl chloride (X) and an alkylenedioxybenzene of the formula:

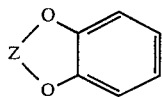
(XI)

wherein Z is as defined in Formula (I) (Org. Syn. Coll. Vol. I, p. 109). In the case where an alkylenedioxybenzene (XI) in which Z is —CH$_2$— is used, that is, in the reaction of 1,3-benzodioxole and an ω-haloalkanoyl chloride, the reaction is preferably carried out at a relatively low temperature because 1,3-benzodioxole is susceptible to decomposition caused by anhydrous aluminum chloride which is used as a Friedel-Craft catalyst. In such cases, the reaction proceeds adequately at a temperature of −20° C. to 0° C., while a reaction temperature of −30° C. to +40° C. is generally employed.

Those compounds of Formula (II) wherein n is 1, i.e., haloacetylalkylenedioxybenzenes may be prepared by reacting an alkylenedioxybenzene (XI) with acetyl chloride and then reacting the resulting acetylalkylenedioxybenzene with a molecular halogen (Org. Syn. Coll. Vol. II, p. 480).

Specific examples of the compounds according to the present invention include:

5-[2-(4-phenyl-1-piperazinyl)acetyl]-1,3-benzodioxole;
5-[2-[4-(4-fluorophenyl)-1-piperazinyl]acetyl]-1,3-benzodioxole;
5-[2-[4-(3-fluorophenyl)-1-piperazinyl]acetyl]-1,3-benzodioxole;
5-[2-[4-(2-fluorophenyl)-1-piperazinyl]acetyl]-1,3-benzodioxole;
5-[2-[4-(4-chlorophenyl)-1-piperazinyl]acetyl]-1,3-benzodioxole;
5-[2-[4-(3-chlorophenyl)-1-piperazinyl]acetyl]-1,3-benzodioxole;
5-[2-[4-(2-chlorophenyl)-1-piperazinyl]acetyl]-1,3-benzodioxole;
5-[2-[4-(3-trifluoromethylphenyl)-1-piperazinyl]acetyl]-1,3-benzodioxole;
5-[2-[4-(4-methoxyphenyl)-1-piperazinyl]acetyl]-1,3-benzodioxole;
5-[2-[4-(3-methoxyphenyl)-1-piperazinyl]acetyl]-1,3-benzodioxole;
5-[2-[4-(2-methoxyphenyl)-1-piperazinyl]acetyl]-1,3-benzodioxole;
5-[2-[4-(4-tolyl)-1-piperazinyl]acetyl]-1,3-benzodioxole;
5-[2-[4-(3-tolyl)-1-piperazinyl]acetyl]-1,3-benzodioxole;
5-[2-[4-(2-tolyl)-1-piperazinyl]acetyl]-1,3-benzodioxole;
5-[2-[4-(2-pyridyl)-1-piperazinyl]acetyl]-1,3-benzodioxole;
6-[2-[4-phenyl-1-piperazinyl)acetyl]-1,4-benzodioxane;
6-[2-[4-(4-fluorophenyl)-1-piperazinyl]acetyl]-1,4-benzodioxane;
6-[2-[4-(3-fluorophenyl)-1-piperazinyl]acetyl]-1,4-benzodioxane;
6-[2-[4-(2-fluorophenyl)-1-piperazinyl]acetyl]-1,4-benzodioxane;
6-[2-[4-(4-chlorophenyl)-1-piperazinyl]acetyl]-1,4-benzodioxane;
6-[2-[4-(3-chlorophenyl)-1-piperazinyl]acetyl]-1,4-benzodioxane;
6-[2-[4-(2-chlorophenyl)-1-piperazinyl]acetyl]-1,4-benzodioxane;
6-[2-[4-(3-trifluoromethylphenyl)-1-piperazinyl]acetyl]-1,4-benzodioxane;
6-[2-[4-(4-methoxyphenyl)-1-piperazinyl]acetyl]-1,4-benzodioxane;
6-[2-[4-(3-methoxyphenyl)-1-piperazinyl]acetyl]-1,4-benzodioxane;
6-[2-[4-(2-methoxyphenyl)-1-piperazinyl]acetyl]-1,4-benzodioxane;
6-[2-[4-(4-tolyl)-1-piperazinyl]acetyl]-1,4-benzodioxane;
6-[2-[4-(3-tolyl)-1-piperazinyl]acetyl]-1,4-benzodioxane;
6-[2-[4-(2-tolyl)-1-piperazinyl]acetyl]-1,4-benzodioxane;
6-[2-[4-(2-pyridyl)-1-piperazinyl]acetyl]-1,4-benzodioxane;
7-[2-(4-phenyl-1-piperazinyl)acetyl]-1,5-benzodioxepin;
7-[2-[4-(4-fluorophenyl)-1-piperazinyl]acetyl]-1,5-benzodioxepine;
7-[2-[4-(3-fluorophenyl)-1-piperazinyl]acetyl]-1,5-benzodioxepine;
7-[2-[4-(2-fluorophenyl)-1-piperazinyl]acetyl]-1,5-benzodioxepine;
7-[2-[4-(4-chlorophenyl)-1-piperazinyl]acetyl]-1,5-benzodioxepine;
7-[2-[4-(3-chlorophenyl)-1-piperazinyl]acetyl]-1,5-benzodioxepine;
7-[2-[4-(2-chlorophenyl)-1-piperazinyl]acetyl]-1,5-benzodioxepine;
7-[2-[4-(3-trifluoromethylphenyl)-1-piperazinyl]acetyl]-1,5-benzodioxepine;
7-[2-[4-(4-methoxyphenyl)-1-piperazinyl]acetyl]-1,5-benzodioxepine;
7-[2-[4-(3-methoxyphenyl)-1-piperazinyl]acetyl]-1,5-benzodioxepine;
7-[2-[4-(2-methoxyphenyl)-1-piperazinyl]acetyl]-1,5-benzodioxepin;
7-[2-[4-(4-tolyl)-1-piperazinyl]acetyl]-1,5-benzodioxepine;
7-[2-[4-(3-tolyl)-1-piperazinyl]acetyl]-1,5-benzodioexpine;
7-[2-[4-(2-tolyl)-1-piperazinyl]acetyl]-1,5-benzodioxepine;
7-[2-[4-(2-pyridyl)-1-piperazinyl]acetyl]-1,5-benzodioxepine;
5-[2-(4-phenyl-1-piperazinyl)-1-hydroxyethyl]-1,3-benzodioxole;
5-[2-[4-(4-fluorophenyl)-1-piperazinyl]-1-hydroxyethyl]-1,3-benzodioxole;
5-[2-[4-(3-fluorophenyl)-1-piperazinyl]-1-hydroxyethyl]-1,3-benzodioxole;
5-[2-[4-(2-fluorophenyl)-1-piperazinyl]-1-hydroxyethyl]-1,3-benzodioxole;
5-[2-[4-(4-chlorophenyl)-1-piperazinyl]-1-hydroxyethyl]-1,3-benzodioxole;
5-[2-[4-(3-chlorophenyl)-1-piperazinyl]-1-hydroxyethyl]-1,3-benzodioxole;
5-[2-[4-(2-chlorophenyl)-1-piperazinyl]-1-hydroxyethyl]-1,3-benzodioxole;
5-[2-[4-(3-trifluoromethylphenyl)-1-piperazinyl]-1-hydroxyethyl]-1,3-benzodioxole;
5-[2-[4-(4-methoxyphenyl)-1-piperazinyl]-1-hydroxyethyl]-1,3-benzodioxole;
5-[2-[4-(3-methoxyphenyl)-1-piperazinyl]-1-hydroxyethyl]-1,3-benzodioxole;
5-[2-[4-(2-methoxyphenyl)-1-piperazinyl]-1-hydroxyethyl]-1,3-benzodioxole;
5-[2-[4-(4-tolyl)-1-piperazinyl]-1-hydroxyethyl]-1,3-benzodioxole;
5-[2-[4-(3-tolyl)-1-piperazinyl]-1-hydroxyethyl]-1,3-benzodioxole;
5-[2-[4-(2-tolyl)-1-piperazinyl]-1-hydroxyethyl]-1,3-benzodioxole;

5-[2-[4-(2-pyridyl)-1-piperazinyl]-1-hydroxyethyl]-1,3-benzodioxole;
6-[2-(4-phenyl-1-piperazinyl)-1-hydroxyethyl]-1,4-benzodioxane;
6-[2-[4-(4-fluorophenyl)-1-piperazinyl]-1-hydroxyethyl]-1,4-benzodioxane;
6-[2-[4-(3-fluorophenyl)-1-piperazinyl]-1-hydroxyethyl]-1,4-benzodioxane;
6-[2-[4-(2-fluorophenyl)-1-piperazinyl]-1-hydroxyethyl]-1,4-benzodioxane;
6-[2-[4-(4-chlorophenyl)-1-piperazinyl]-1-hydroxyethyl]-1,4-benzodioxane;
6-[2-[4-(3-chlorophenyl)-1-piperazinyl]-1-hydroxyethyl]-1,4-benzodioxane;
6-[2-[4-(2-chlorophenyl)-1-piperazinyl]-1-hydroxyethyl]-1,4-benzodioxane;
6-[2-[4-(3-trifluoromethylphenyl)-1-piperazinyl]-1-hydroxyethyl]-1,4-benzodioxane;
6-[4-[4-(4-methoxyphenyl)-1-piperazinyl]-1-hydroxyethyl]-1,4-benzodioxane;
6-[2-[4-(3-methoxyphenyl)-1-piperazinyl]-1-hydroxyethyl]-1,4-benzodioxane;
6-[2-[4-(2-methoxyphenyl)-1-piperazinyl]-1-hydroxyethyl]-1,4-benzodioxane;
6-[2-[4-(4-tolyl)-1-piperazinyl]-1-hydroxyethyl]-1,4-benzodioxane;
6-[2-[4-(3-tolyl)-1-piperazinyl]-1-hydroxyethyl]-1,4-benzodioxane;
6-[2-[4-(2-tolyl)-1-piperazinyl]-1-hydroxyethyl]-1,4-benzodioxane;
6-[2-[4-(2-pyridyl)-1-piperazinyl]-1-hydroxyethyl]-1,4-benzodioxane;
7-[2-(4-phenyl-1-piperazinyl)-1-hydroxyethyl]-1,5-benzodioxepine;
7-[2-[4-(4-fluorophenyl)-1-piperazinyl]-1-hydroxyethyl]-1,5-benzodioxepine;
7-[2-[4-(3-fluorophenyl)-1-piperazinyl]-1-hydroxyethyl]-1,5-benzodioxepine;
7-[2-[4-(2-fluorophenyl)-1-piperazinyl]-1-hydroxyethyl]-1,5-benzodioxepine;
7-[2-[4-(4-chlorophenyl)-1-piperazinyl]-1-hydroxyethyl]-1,5-benzodioxepine;
7-[2-[4-(4-chlorophenyl)-1-piperazinyl]-1-hydroxyethyl]-1,5-benzodioxepine;
7-[2-[4-(2-chlorophenyl)-1-piperazinyl]-1-hydroxyethyl]-1,5-benzodioxepine;
7-[2-[4-(3-trifluoromethylphenyl)-1-piperazinyl]-1-hydroxyethyl]-1,5-benzodioxepine;
7-[2-[4-(4-methoxyphenyl)-1-piperazinyl]-1-hydroxyethyl]-1,5-benzodioxepine;
7-[2-[4-(3-methoxyphenyl)-1-piperazinyl]-1-hydroxyethyl]-1,5-benzodioxepine;
7-[2-[4-(2-methoxyphenyl)-1-piperazinyl]-1-hydroxyethyl]-1,5-benzodioxepine;
7-[2-[4-(4-tolyl)-1-piperazinyl]-1-hydroxyethyl]-1,5-benzodioxepine;
7-[2-[4-(3-tolyl)-1-piperazinyl]-1-hydroxyethyl]-1,5-benzodioxepine;
7-[2-[4-(2-tolyl)-1-piperazinyl]-1-hydroxyethyl]-1,5-benzodioxepine;
7-[2-[4-(2-pyridyl9-1-piperazinyl]-1-hydroxyethyl]-1,5-benzodioxepine;

The above examples are exemplary of those compounds of Formula (I) wherein n is 1, Z is —(CH$_2$)$_m$— where m is an integer of 1 to 3 and Y is

or —CH(OH)—. Similarly, their respective corresponding compounds in which n is an integer of 2 to 6 are also illustrative of the compounds of this invention.

The following are examples of those compounds of Formula (I) wherein Z is —CH$_2$C(CH$_3$)$_2$CH$_2$— and n is 1:

7-[2-(4-phenyl-1-piperazinyl)acetyl]-3,3-dimethyl-1,5-benzodioxepine;
7-[2-[4-(4-fluorophenyl)-1-piperazinyl]acetyl]-3,3-dimethyl-1,5-benzodioxepine;
7-[2-[4-(3-fluorophenyl)-1-piperazinyl]acetyl]-3,3-dimethyl-1,5-benzodioxepine;
7-[2-[4-(2-fluorophenyl)-1-piperazinyl]acetyl]-3,3-dimethyl-1,5-benzodioxepine;
7-[2-[4-(4-chlorophenyl)-1-piperazinyl]acetyl]-3,3-dimethyl-1,5-benzodioxepine;
7-[2-[4-(3-chlorophenyl)-1-piperazinyl]acetyl]-3,3-dimethyl-1,5-benzodioxepine;
7-[2-[4-(2-chlorophenyl)-1-piperazinyl]acetyl]-3,3-dimethyl-1,5-benzodioxepine;
7-[2-[4-(3-trifluoromethylphenyl)-1-piperazinyl]acetyl]-3,3-dimethyl-1,5-benzodioxepine;
7-[2-[4-(4-methoxyphenyl)-1-piperazinyl]acetyl]-3,3-dimethyl-1,5-benzodioxepine;
7-[2-[4-(3-methoxyphenyl)-1-piperazinyl]acetyl]-3,3-dimethyl-1,5-benzodioxepine;
7-[2-[4-(2-methoxyphenyl)-1-piperazinyl]acetyl]-3,3-dimethyl-1,5-benzodioxepine;
7-[2-[4-(4-tolyl)-1-piperazinyl]acetyl]-3,3-dimethyl-1,5-benzodioxepine;
7-[2-[4-(3-tolyl)-1-piperazinyl]acetyl]-3,3-dimethyl-1,5-benzodioxepine;
7-[2-[4-(2-tolyl)-1-piperazinyl]acetyl]-3,3-dimethyl-1,5-benzodioxepine;
7-[2-[4-(2-pyridyl)-1-piperazinyl]acetyl]-3,3-dimethyl-1,5-benzodioxepine;
7-[2-(4-phenyl-1-piperazinyl)-1-hydroxyethyl]-3,3-dimethyl-1,5-benzodioxepine;
7-[2-[4-(4-fluorophenyl)-1-piperazinyl]-1-hydroxyethyl]-3,3-dimethyl-1,5-benzodioxepine;
7-[2-[4-(3-fluorophenyl)-1-piperazinyl]-1-hydroxyethyl]-3,3-dimethyl-1,5-benzodioxepine;
7-[2-[4-(2-fluorophenyl)-1-piperazinyl]-1-hydroxyethyl]-3,3-dimethyl-1,5-benzodioxepine;
7-[2-[4-(4-chlorophenyl)-1-piperazinyl]-1-hydroxyethyl]-3,3-dimethyl-1,5-benzodioxepine;
7-[2-[4-(3-chlorophenyl)-1-piperazinyl]-1-hydroxyethyl]-3,3-dimethyl-1,5-benzodioxepine;
7-[2-[4-(2-chlorophenyl)-1-piperazinyl]-1-hydroxyethyl]-3,3-dimethyl-1,5-benzodioxepine;
7-[2-[4-(3-trifluoromethylphenyl)-1-piperzinyl]-1-hydroxyethyl]-3,3-dimethyl-1,5-benzodioxepine;
7-[2-[4-(4-methoxyphenyl)-1-piperazinyl]-1-hydroxyethyl]-3,3-dimethyl-1,5-benzodioxepine;
7-[2-[4-(3-methoxyphenyl)-1-piperazinzyl]-1-hydroxyethyl]-3,3-dimethyl-1,5-benzodioxepine;
7-[2-[4-(2-methoxyphenyl)-1-piperazinyl]-1-hydroxyethyl]-3,3-dimethyl-1,5-benzodioxepin;
7-[2-[4-(4-tolyl)-1-piperazinyl]-1-hydroxyethyl]-3,3-dimethyl-1,5-benzodioxepin;
7-[2-[4-(3-tolyl)-1-piperazinyl]-1-hydroxyethyl]-3,3-dimethyl-1,5-benzodioxepin;

7-[2-[4-(2-tolyl)-1-piperazinyl]-1-hydroxyethyl]-3,3-dimethyl-1,5-benzodioxepin;

7-[2-[4-(2-pyridyl)-1-piperazinyl]-1-hydroxyethyl]-3,3-dimethyl-1,5-benzodioxepin;

Similarly, these respective corresponding compounds in which n is an integer of 2 to 6 and/or Z is —CH$_2$CH(CH$_3$)CH$_2$— are also illustrative of the compounds of this invention.

The following are examples of those compounds of Formula (I) wherein Z is —CH$_2$—, n is 1 and Y is

where R$_3$ is hydrogen:

N-[2-(4-phenyl-1-piperazinyl)ethyl]-3,4-methylenedioxyaniline;
N-[2-[4-(4-fluorophenyl)-1-piperazinyl]ethyl]-3,4-methylenedioxyaniline;
N-[2-[4-(3-fluorophenyl)-1-piperazinyl]ethyl]-3,4-methylenedioxyaniline;
N-[2-[4-(2-fluorophenyl)-1-piperazinyl]ethyl]-3,4-methylenedioxyaniline;
N-[2-[4-(4-chlorophenyl)-1-piperazinyl]ethyl]-3,4-methylenedioxyaniline;
N-[2-[4-(3-chlorophenyl)-1-piperazinyl]ethyl]-3,4-methylenedioxyaniline;
N-[2-[4-(2-chlorophenyl)-1-piperazinyl]ethyl]-3,4-methylenedioxyaniline;
N-[2-[4-(3-trifluoromethylphenyl)-1-piperazinyl]ethyl]-3,4-methylenedioxyaniline;
N-[2-[4-(4-methoxyphenyl)-1-piperazinyl]ethyl]-3,4-methylenedioxyaniline;
N-[2-[4-(3-methoxyphenyl)-1-piperazinyl]ethyl]-3,4-methylenedioxyaniline;
N-[2-[4-(2-methoxyphenyl)-1-piperazinyl]ethyl]-3,4-methylenedioxyaniline;
N-[2-[4-(4-tolyl)-1-piperazinyl]ethyl]-3,4-methylenedioxyaniline;
N-[2-[4-(3-tolyl)-1-piperazinyl]ethyl]-3,4-methylenedioxyaniline;
N-[2-[4-(2-tolyl)-1-piperazinyl]ethyl]-3,4-methylenedioxyaniline;
N-[2-[4-(2-pyridyl)-1-piperazinyl]ethyl]-3,4-methylenedioxyaniline.

The respective corresponding compounds of these in which Z is —(CH$_2$)$_m$ where m is 2 and 3, n is an integer of 2 to 6 and/or Y is

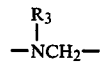

where R$_3$ is methyl and acetyl are also illustrative of the compounds of this invention.

Among the above compounds, the preferred compounds are as follows:

5-[2-(4-phenyl-1-piperazinyl)-1-hydroxyethyl]-1,3-benzodioxole
5-[2-[4-(2-methoxyphenyl)-1-piperazinyl]-1-hydroxyethyl]-1,3-benzodioxole
5-[4-(4-phenyl-1-piperazinyl)-1-hydroxybutyl]-1,3-benzodioxole
6-[4-(4-phenyl-1-piperazinyl)-1-hydroxybutyl]-1,4-benzodioxane
7-[4-(4-phenyl-1-piperazinyl)-1-hydroxybutyl]-1,5-benzodioxepine
5-[4-[4-(2-pyridyl)-1-piperazinyl]-1-hydroxybutyl]-1,3-benzodioxole
6-[4-[4-(2-pyridyl)-1-piperazinyl]-1-hydroxybutyl]-1,4-benzodioxane
7-[4-[4-(2-pyridyl)-1-piperazinyl]-1-hydroxybutyl]-1,5-benzodioxepine
5-[4-[4-(2-methoxyphenyl)-1-piperazinyl]-1-hydroxybutyl]-1,3-benzodioxole
6-[4-[4-(2-methoxyphenyl)-1-piperazinyl]-1-hydroxybutyl]-1,4-benzodioxane
7-[4-[4-(2-methoxyphenyl)-1-piperazinyl]-1-hydroxybutyl]-1,5-benzodioxepine
5-[5-(4-phenyl-1-piperazinyl)-1-hydroxypentyl]-1,3-benzodioxole
6-[5-(4-phenyl-1-piperazinyl)-1-hydroxypentyl]-1,4-benzodioxane
7-[5-(4-phenyl-1-piperazinyl)-1-hydroxypentyl]-1,5-benzodioxepine
7-[5-[4-(2-methoxyphenyl)-1-piperazinyl]-1-hydroxypentyl]-1,5-benzodioxepine
5-[4-(4-phenyl-1-piperazinyl)butyryl]-1,3-benzodioxole
6-[4-(4-phenyl-1-piperazinyl)butyryl]-1,4-benzodioxane
7-[4-(4-phenyl-1-piperazinyl)butyryl]-1,5-benzodioxepine
5-[4-[4-(2-pyridyl)-1-piperazinyl]butyryl]-1,3-benzodioxole
6-[4-[4-(2-pyridyl)-1-piperazinyl]butyryl]-1,4-benzodioxane
7-[4-[4-(2-pyridyl)-1-piperazinyl]butyryl]-1,5-benzodioxepine
5-[4-[4-(2-methoxyphenyl)-1-piperazinyl]butyryl]-1,3-benzodioxole
6-[4-[4-(2-methoxyphenyl)-1-piperazinyl]butyryl]-1,4-benzodioxane
7-[4-[4-(2-methoxyphenyl)-1-piperazinyl]butyryl]-1,5-benzodioxepine
5-[5-(4-phenyl-1-piperazinyl]valeryl]-1,3-benzodioxole
6-[5-(4-phenyl-1-piperwzinyl)valeryl]-1,4-benzodioxane
7-[5-(4-phenyl-1-piperazinyl)valeryl]-1,5-benzodioxepine
6-[5-[4-(2-chlorophenyl)-1-piperazinyl]valeryl]-1,4-benzodioxane
5-[5-[4-(2-methoxyphenyl)-1-piperazinyl]valeryl]-1,3-benzodioxole
6-[5-[4-(2-methoxyphenyl)-1-piperazinyl]varleryl]-1,4-benzodioxane
7-[5-[4-(2-methoxyphenyl-1-piperazinyl]valeryl]-1,5-benzodioxepine
7-[5-[4-(2-pyridyl)-1-piperazinyl]valeryl]-1,5-benzodioxepine
7-[5-[4-(2-methoxyphenyl)-1-piperazinyl]valeryl]-3,3-dimethyl-1,5-benzodioxepine
N-[2-[4-(2-methoxyphenyl)-1-piperazinyl]ethyl]-N-acetyl-3,4-methylenedioxyaniline The present invention also embraces acid addition salts of the alkylenedioxybenzene derivatives of Formula (I). The acids that can be used to form such addition salts include inorganic acids such as hydrochloric acid, hydrobromic acid, sulfuric acid, phosphoric acid, nitric acid, etc. as well as organic acids such as acetic acid, succinic acid, adipic acid, propionic acid, tartaric acid, fumaric acid, maleic acid, oxalic acid, citric acid, benzoic acid, toluenesulfonic acid, methanesulfonic acid, etc.

As previously mentioned, the compounds of this invention possess hypotensive activities.

The hypotensive activities of the compounds of this invention were tested as follows: The test animals used were spontaneous hypertensive rats (SHR) of 5 to 7 month old weighing 300 to 370 g. The blood pressure and the heart rate were measured bloodily under no anesthesia by means of a catheter which has been inserted through the tail's artery under ether anesthesia, thereby determining the average blood pressure and heart rate before medication.

Thereafter, the test compound was orally administered every hour at a dose of 1, 3 or 10 mg/kg and the hypotensive effect was evaluated. The hypotensive effect was expressed as percent drop relative to the blood pressure before medication. The results are shown in Table 1.

The values for acute toxicity ($LD_{50}$) were calculated by the Litchfield-Wilcoxon method from the data obtained on mice. The results are shown in Table 2.

As can be seen from Table 1, all the compounds of this invention exert their hypotensive effects satisfactorily at an oral dose of 1 mg/kg and they develop their efficacy rapidly and have long-lasting effects. In addition, as shown in Table 2, the acute toxicity of the compounds is weak. Therefore, in view of their high efficacy developed, it is inferred that they are medicaments of very high safety.

TABLE 1

| | Hypotensive effect (average % drop in blood pressure) | | |
|---|---|---|---|
| No.* | 1 mg/kg p.o. | 3 mg/kg p.o. | 10 mg/kg p.o. |
| 2 | 10.2 | 19.2 | 36.5 |
| 8 | 8.6 | 14.1 | 25.0 |
| 16 | 7.9 | 11.9 | 29.8 |
| 17 | 8.1 | 20.5 | 53.1 |
| 19 | 12.8 | 45.9 | 56.6 |
| 20 | 13.7 | 38.4 | 56.1 |
| 21 | 19.8 | 30.9 | 43.4 |
| 25 | 30.3 | 35.8 | 43.9 |
| 26 | 13.0 | 21.9 | 52.6 |
| 29 | 10.8 | 27.5 | 50.7 |
| 31 | 11.5 | 33.6 | 45.7 |
| 33 | 22.6 | 41.8 | 43.2 |
| 34 | 24.5 | 40.4 | 48.0 |
| 36 | 10.1 | 19.4 | 31.0 |
| 37 | 15.6 | 30.4 | 45.7 |
| 51 | 5.9 | 14.5 | 49.9 |
| 56 | 6.2 | 17.0 | 31.5 |
| 58 | 12.7 | 51.6 | 62.7 |
| 59 | 9.8 | 34.4 | 40.5 |
| 64 | 10.1 | 21.3 | 54.5 |
| 65 | 21.7 | | |
| 68 | 12.5 | 28.6 | 44.0 |
| 69 | 23.8 | | |
| 71 | 11.5 | 20.9 | 43.1 |
| 72 | 10.1 | 25.3 | 46.4 |
| 74 | 29.9 | | |
| 76 | 8.6 | 23.7 | 56.7 |
| 77 | 12.9 | 21.5 | 34.5 |
| 78 | 13.7 | 24.9 | 27.8 |
| 79 | 8.0 | 15.8 | 32.5 |
| 81 | 15.5 | 21.2 | |

*The compound numbers are the same as those in Table 3 and the structure of each compound is shown therein.

TABLE 2

| | Acute toxicity ($LD_{50}$) |
|---|---|
| No.* | $LD_{50}$ (mice, mg/kg i.v.) |
| 21 | 184.0 (152.3–222.3) |
| 25 | 68.5 (61.6–76.2) |
| 64 | 45.7 (40.7–51.3) |

*The compound numbers are the same as those given in Table 3 and the structure of each compound is shown therein.

The compounds according to this invention may be administered by any route and both of oral administration and parenteral administration such as subcutaneous injection, intravenous injection, intramuscular injection or intraperitoneal injection are possible.

The dosage may be determined depending on the age, condition and weight of the patient, the type of the concurrent treatment, if any, the frequency of the treatment, the nature of the desired effect, etc.

In general, the daily dose of the active ingredient is 0.1 to 100 mg/kg-body weight, usually 1 to 30 mg/kg-body weight which is administered in one or more portions.

For oral administration, the compounds of this invention are applied in the form of tablets, capsules, dusts, solutions, elixirs or the like, while for parenteral administration they are applied in sterized liquid forms such as solutions or suspensions. Whey they are used in the above-mentioned dosage forms, a solid or liquid, non-toxic pharmaceutical carrier may be incorporated in the formulations.

An example of the solid carriers is conventional gelatine capsules. The active ingredients may be tabletted or dustpackaged with or without an adjuvant.

These capsules, tablets or dusts contain generally 5 to 95%, preferably 25 to 90% by weight of the active ingredient. Thus, each of these dosage forms may contain 5 to 500 mg, preferably 25 to 250 mg of the active ingredient.

Useful liquid carriers include water, oils of animal or vegetable origin such as petroleum, peanut oil, soybean oil, mineral oil, sesame oil, and synthetic oils.

In addition, physiological saline, solutions of dextrose or similar sugar and glycols such as ethylene glcol, propylene glycol, polyethylene glycol, etc. are generally suitable for use as liquid carriers. Particularly, injections in which physiological saline is used as carriers usually contain 0.5 to 20%, preferably 1 to 10% by weight of the active ingredient.

Liquid preparations for oral administration are preferably suspensions or syrups containing 0.5 to 10% by weight of the active ingredient. In such cases, water-like excipients such as flavors, syrups, pharmaceutical micelles may be used as carriers.

As stated above, the compounds of this invention are valuable as hypotensives.

Having generally described the invention, a more complete understanding can be obtained by reference to certain specific examples, which are included for purposes of illustration only and are not intended to be limiting unless otherwise specified.

EXAMPLE 1

5-[3-(4-Phenyl-1-piperazinyl)propionyl]-1,3-benzodioxole

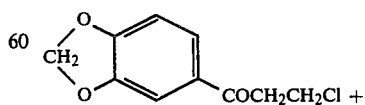

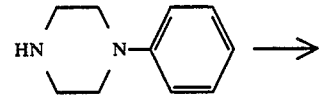

-continued

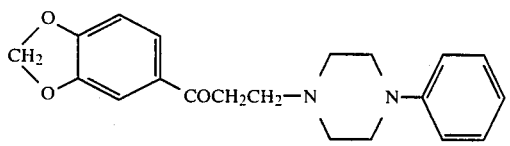

5-(3-Chloropropionyl)-1,3-benzodioxole (3 g) and N-phenylpiperazine (2.4 g) were dissolved in DMF (20 ml), triethylamine (1.7 g) was then added and the mixture was stirred for 10 hours at room temperature. After completion of the reaction, the reaction mixture was poured into water and extracted with ethyl acetate. The extract was dried over anhydrous sodium sulfate and the solvent was distilled off. The residue was crystallized from methanol and the resulting crystals were recrystallized from ethanol to give 5-[3-(4-phenyl-1-piperazinyl)propionyl]-1,3-benzodioxole (4.0 g, 84% yield). The characteristics of this compound are shown in Table 3 as Compound 47.

In order to prepare the hydrochloride of this compound, the extract was concentrated and the residue was dissolved in ethyl acetate. To the solution was added 20% hydrogen chloride in ethanol and the resulting precipitate was collected by filtration and recrystallized from ethanol, yielding the desired hydrochloride.

EXAMPLE 2

5-[4-(4-Phenyl-1-piperazinyl)butyryl]-1,3-benzodioxole dihydrochloride

To 5-(4-chlorobutyryl)-1,3-benzodioxole (4.0 g) and N-phenylpiperazine (3.0 g) dissolved in DMF (25 ml) was added triethylamine (2.2 g) and the mixture was heated at 80° C. for 40 hours under stirring. After completion of the reaction, the reaction mixture was poured into water and extracted with ethyl acetate. The extract was dried over anhydrous sodium sulfate and the solvent was distilled off. The residue was dissolved in ethyl acetate and 20% hydrogen chloride in ethanol (6.5 ml) was added. The resulting crystals were collected by filtration and recrystallized from ethanol to give 5-[4-phenyl-1-piperazinyl)butyryl]-1,3-benzodioxole dihydrochloride (5.1 g, 68% yield). The characteristics of this compound are shown in Table 3 as Compound 57.

EXAMPLE 3

5-[3-(4-Phenyl-1-piperazinyl)-1-hydroxypropyl]-1,3-benzodioxole

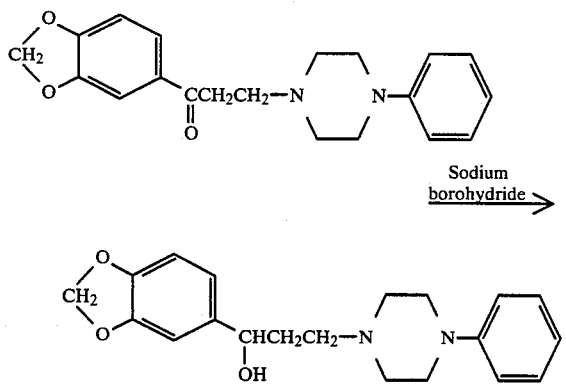

5-[3-(4-Phenyl-1-piperazinyl)propionyl]-1,3-benzodioxole (4.0 g) as prepared in Example 1 was suspended in methanol (50 ml) and sodium borohydride (0.5 g) was added. The mixture was allowed to react for 10 hours at room temperature and after completion of the reaction it was evaporated in vacuo. The residue was extracted with ethyl acetate and the extract was washed with saturated saline and dried over anhydrous sodium sulfate. The solvent was then distilled off and the residue was crystallized from methanol to give 5-[3-(4-phenyl-1-piperazinyl)-1-hydroxypropyl]-1,3-benzodioxole (3.6 g, 75% yield). The characteristics of this compound are shown in Table 3 as Compound 9.

EXAMPLE 4

5-[4-(4-Phenyl-1-piperazinyl)-1-hydroxybutyl]-1,3-benzodioxole dihydrochloride

5-[4-(4-Phenyl-1-piperazinyl)butyryl]-1,3-benzodioxole dichloride (3.8 g) as prepared in Example 2 was suspended in methanol (50 ml) and 2N sodium hydroxide solution (4.5 ml) and then sodium borohydride (0.5 g) were added. The mixture was stirred for 10 hours at room temperature and the solvent was then distilled off. The residue was extracted with ethyl acetate and the extract was washed with saturated saline and dried over anhydrous sodium sulfate. Thereafter, 20% hydrogen chloride in ethanol (4.9 ml) was added and the resulting crystals were collected by filtration and recrystallized from ethanol to give 5-[4-(4-phenyl-1-piperazinyl)-1-hydroxybutyl]-1,3-benzodioxole dihydrochloride (3.5 g, 62% yield). The characteristics of this compound are shown in Table 3 as Compound 19.

EXAMPLE 5

N-[3-(4-Phenyl-1-piperazinyl)propyl]-3,4-methylenedioxyaniline trihydrochloride

To N-(3-chloropropionyl)-3,4-methylenedioxyaniline (2.0 g) dissolved in N,N-dimethylformamide (20 ml) were added N-phenylpiperazine (1.6 g) and triethylamine (3 ml) and the mixture was stirred at 80° C. for 20 hours in a nitrogen atmosphere. The reaction mixture was evaporated in vacuo and to the residue were added ethyl acetate and 2N sodium hydroxide solution. After the aqueous layer was removed, the ethyl acetate layer was washed twice with water and dried over anhydrous sodium sulfate. The ethyl acetate was then distilled off and the residual solid was recrystallized from ethanol to give N-[3-(4-phenyl-1-piperazinyl)propionyl]-3,4-methylenedioxyaniline (3.4 g, 90% yield).

Subsequently, to a suspension of lithium aluminum hydride (0.6 g) in tetrahydrofuran (20 ml) was added dropwise under stirring a solution of N-[3-(4-phenyl-1-piperazinyl)-propionyl]-3,4-methylenedioxyaniline (2 g) in tetrahydrofuran (20 ml) and after completion of the dropwise addition the mixture was heated at reflux for 3 hours. Upon cooling, the reaction mixture was worked up in a conventional manner and the precipitated aluminum hydroxide was filtered off. The filtrate was evaporated in vacuo and the residue was purified by chromatography on silica gel. The collected syrup was dissolved in ethyl acetate and 20% hydrogen chloride in ethyl acetate was then added with stirring under ice cooling. The resulting crystals were collected by filtration and recrystallized from ethanol to give N-[3-(4-phenyl-1-piperazinyl)propyl]-3,4-methylenedioxyaniline trichloride (1.9 g, 74.8% yield). The characteristics of this compound are shown in Table 3 as Compound 79.

EXAMPLE 6

N-[2-[4-(2-methoxyphenyl)-1-piperazinyl]ethyl]-N-acetyl-3,4-methylenedioxyaniline hydrochloride Free N-[2-[4-(2-methoxyphenyl)-1-piperazinyl]ethyl]-3,4-methylenedioxyaniline (2.0 g) prepared in accordance with the procedure described in Example 5 was dissolved in pyridine (4 ml) and acetic anhydride (2 ml) was added. The mixture was stirred for 4 hours at room temperature and the solvent was then distilled off. The residue was extracted with ether and the extract was washed with saturated saline and dried over anhydrous sodium sulfate. A solution of hydrogen chloride in ethyl acetate was then added and the resulting crystals were collected by filtration and recrystallized from ethanol to give N-[2-[4-(2-methoxyphenyl)-1-piperazinyl]-ethyl]-N-acetyl-3,4-methylenedioxyaniline hydrochloride (1.9 g, 72% yield). The characteristics of this compound are shown in Table 3 as Compound 81.

Other compounds according to this invention were prepared in the same manner as described in the preceding examples and their characteristics are also shown in Table 3.

TABLE 3

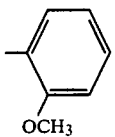

| No. | Z | Y | n | R | Addition salt | M.P. (°C.) | Elementary analysis C, H, N Calc. | ; Found | |
|---|---|---|---|---|---|---|---|---|---|
| 1 | —CH$_2$— | CH(OH) | 1 | Ph* | — | 137–8 | 69.92, 6.79, 8.58 | ; 70.21, 6.85, | 8.43 |
| 2 | —CH$_2$— | CH(OH) | 1 | 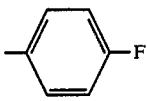 | — | 121–2 | 67.39, 6.79, 7.86 | ; 67.18, 6.88, | 7.97 |
| 3 | —(CH$_2$)$_2$— | CH(OH) | 1 | Ph | — | 172–4 | 70.56, 7.11, 8.23 | ; 70.42, 7.21, | 8.09 |
| 4 | —(CH$_2$)$_2$— | CH(OH) | 1 | 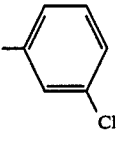 | — | 195–6 | 64.16, 6.19, 7.48 | ; 64.23, 6.20, | 7.55 |
| 5 | —(CH$_2$)$_2$— | CH(OH) | 1 | 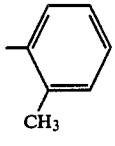 | — | 175–7 | 61.46, 5.93, 7.17 | ; 61.59, 6.08, | 7.25 |
| 6 | —(CH$_2$)$_2$— | CH(OH) | 1 | 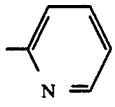 | (CO$_2$H)$_2$ | 193–6 | 62.15, 6.35, 6.30 | ; 62.43, 6.49, | 6.21 |
| 7 | —(CH$_2$)$_2$— | CH(OH) | 1 | 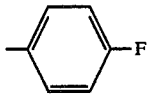 | — | 173–5 | 66.84, 6.79, 12.31 | ; 66.68, 6.70, | 12.44 |
| 8 | —(CH$_2$)$_3$— | CH(OH) | 1 | Ph | — | 168–9 | 71.16, 7.39, 7.90 | ; 71.29, 7.45, | 7.79 |
| 9 | —CH$_2$— | CH(OH) | 2 | Ph | — | 131–2 | 70.56, 7.11, 8.23 | ; 70.31, 7.23, | 8.09 |
| 10 | —CH$_2$— | CH(OH) | 2 | 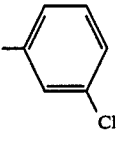 | Maleate | 167–8 | 60.75, 5.74, 5.90 | ; 60.84, 5.58, | 6.01 |
| 11 | —CH$_2$— | CH(OH) | 2 | 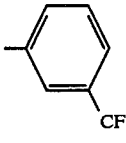 | " | 104–5 | 57.25, 5.19, 5.34 | ; 57.42, 5.28, | 5.30 |

TABLE 3-continued

Structure: benzene ring with Z bridging two O atoms on one side (forming fused ring), and on the other side Y—(CH$_2$)$_n$—N (piperazine) N—R

| No. | Z | Y | n | R | Addition salt | M.P. (°C.) | Elementary analysis C, H, N Calc. | ; | Found |
|---|---|---|---|---|---|---|---|---|---|
| 12 | —(CH$_2$)$_2$— | CH(OH) | 2 | Ph | — | 115–6 | 71.16, 7.39, 7.90 | ; | 71.01, 7.45, 7.79 |
| 13 | —(CH$_2$)$_2$— | CH(OH) | 2 | 3-F-C$_6$H$_4$ | — | 127–8 | 67.72, 6.77, 7.52 | ; | 67.49, 6.89, 7.63 |
| 14 | —(CH$_2$)$_2$— | CH(OH) | 2 | 4-Cl-C$_6$H$_4$ | Maleate | 110–2 | 59.46, 5.79, 5.55 | ; | 59.67, 5.63, 5.49 |
| 15 | —(CH$_2$)$_2$— | CH(OH) | 2 | 3-Cl-C$_6$H$_4$ | " | 131–4 | 59.46, 5.79, 5.55 | ; | 59.55, 5.70, 5.67 |
| 16 | —(CH$_2$)$_2$— | CH(OH) | 2 | 2-Cl-C$_6$H$_4$ | — | 120–1 | 64.86, 6.48, 7.20 | ; | 65.01, 6.43, 7.31 |
| 17 | —(CH$_2$)$_2$— | CH(OH) | 2 | 2-OCH$_3$-C$_6$H$_4$ | — | 140–2 | 68.72, 7.34, 7.29 | ; | 68.79, 7.41, 7.20 |
| 18 | —(CH$_2$)$_3$— | CH(OH) | 2 | Ph | — | 156–8 | 71.71, 7.66, 7.60 | ; | 71.91, 7.60, 7.48 |
| 19 | —CH$_2$— | CH(OH) | 3 | Ph | 2HCl | 202–5 | 59.02, 6.60, 6.55 | ; | 58.79, 6.51, 6.42 |
| 20 | —(CH$_2$)$_2$— | CH(OH) | 3 | Ph | — | 117–8 | 71.71, 7.66, 7.60 | ; | 71.63, 7.71, 7.57 |
| 21 | —(CH$_2$)$_3$— | CH(OH) | 3 | Ph | — | 111–3 | 72.22, 7.91, 7.32 | ; | 72.42, 7.94, 7.51 |
| 22 | —(CH$_2$)$_3$— | CH(OH) | 3 | 4-F-C$_6$H$_4$ | — | 130–1 | 68.98, 7.30, 6.99 | ; | 68.81, 7.42, 7.08 |
| 23 | —(CH$_2$)$_3$— | CH(OH) | 3 | 3-CF$_3$-C$_6$H$_4$ | — | 132–4 | 63.99, 6.49, 6.22 | ; | 64.23, 6.55, 6.30 |
| 24 | —(CH$_2$)$_3$— | CH(OH) | 3 | 4-OCH$_3$-C$_6$H$_4$ | — | 118–120 | 69.88, 7.82, 6.79 | ; | 69.97, 7.75, 6.70 |
| 25 | —(CH$_2$)$_3$— | CH(OH) | 3 | 2-pyridyl | — | 126–7 | 68.90, 7.62, 10.96 | ; | 68.78, 7.56, 10.84 |
| 26 | —CH$_2$— | CH(OH) | 4 | Ph | — | 111–113 | 71.71, 7.66, 7.60 | ; | 71.93, 7.81, 7.55 |
| 27 | —(CH$_2$)$_2$— | CH(OH) | 4 | Ph | — | 120–2 | 72.22, 7.91, 7.32 | ; | 72.03, 8.04, 7.38 |

TABLE 3-continued

[Structure: Z bridges two O's on benzene ring connected to Y—(CH$_2$)$_n$—N-piperazine-N—R]

| No. | Z | Y | n | R | Addition salt | M.P. (°C.) | Calc. C, H, N | ; | Found C, H, N |
|---|---|---|---|---|---|---|---|---|---|
| 28 | —(CH$_2$)$_2$— | CH(OH) | 4 | 4-F-C$_6$H$_4$ | — | 92–3 | 68.98, 7.30, 6.99 | ; | 69.17, 7.45, 7.08 |
| 29 | —(CH$_2$)$_3$— | CH(OH) | 4 | Ph | — | 124–6 | 72.69, 8.13, 7.07 | ; | 72.53, 8.02, 6.96 |
| 30 | —(CH$_2$)$_2$— | CH(OH) | 5 | Ph | — | 121–2 | 72.69, 8.13, 7.07 | ; | 72.85, 8.21, 7.23 |
| 31 | —CH$_2$— | CH(OH) | 3 | 2-pyridyl | — | 82–2 | 67.58, 7.09, 11.82 | ; | 67.44, 7.00, 11.94 |
| 32 | —CH$_2$— | CH(OH) | 3 | 2-OCH$_3$-C$_6$H$_4$ | — | 155–6.5 | 68.73, 7.34, 7.29 | ; | 68.89, 7.25, 7.43 |
| 33 | —(CH$_2$)$_2$— | CH(OH) | 3 | " | — | 108–110 | 69.32, 7.59, 7.03 | ; | 69.19, 7.43, 7.13 |
| 34 | —(CH$_2$)$_3$— | CH(OH) | 3 | " | 2HCl | 146–50 | 59.38, 7.06, 5.77 | ; | 59.17, 6.92, 5.69 |
| 35 | —(CH$_2$)$_2$— | CH(OH) | 3 | 2-pyridyl | — | 78–9 | 68.27, 7.37, 11.37 | ; | 68.41, 7.33, 11.19 |
| 36 | —(CH$_2$)$_3$— | CH(OH) | 4 | " | — | 127–9 | 69.49, 7.86, 10.57 | ; | 69.36, 7.72, 10.64 |
| 37 | —(CH$_2$)$_3$— | CH(OH) | 4 | 2-OCH$_3$-C$_6$H$_4$ | 2HCl | 136–8 | 60.12, 7.26, 5.61 | ; | 60.21, 7.40, 5.54 |
| 38 | —CH$_2$C(CH$_3$)$_2$CH$_2$— | CH(OH) | 4 | " | " | 124–8 | 61.47, 7.64, 5.31 | ; | 61.32, 7.72, 5.32 |
| 39 | —CH$_2$— | —CO— | 1 | Ph | — | 169–171 | 70.35, 6.22, 8.64 | ; | 70.22, 6.30, 8.55 |
| 40 | —CH$_2$— | " | 1 | 2-OCH$_3$-C$_6$H$_4$ | — | 122 | 67.78, 6.26, 7.91 | ; | 67.91, 6.21, 8.03 |
| 41 | —(CH$_2$)$_2$— | " | 1 | Ph | 2HCl | 131–5 | 58.40, 5.88, 6.81 | ; | 58.23, 5.96, 6.67 |
| 42 | —(CH$_2$)$_2$— | " | 1 | 4-F-C$_6$H$_4$ | " | 174–8 | 55.95, 5.40, 6.53 | ; | 56.21, 5.49, 6.41 |
| 43 | —(CH$_2$)$_2$— | " | 1 | 4-Cl-C$_6$H$_4$ | " | 169–173 | 53.89, 5.20, 6.28 | ; | 53.68, 5.37, 6.43 |

TABLE 3-continued
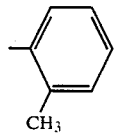
| No. | Z | Y | n | R | Addition salt | M.P. (°C.) | Elementary analysis C, H, N Calc. | ; | Found | |
|---|---|---|---|---|---|---|---|---|---|---|
| 44 | —(CH₂)₂— | " | 1 | 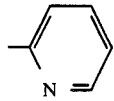 | " | 193–6 | 59.30, 6.16, | 6.59 ; | 59.50, 6.21, | 6.55 |
| 45 | —(CH₂)₂— | " | 1 | 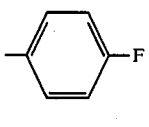 | 3HCl | 148–152 | 50.85, 5.39, | 9.36 ; | 50.99, 5.31, | 9.42 |
| 46 | —(CH₂)₃— | " | 1 | Ph | 2HCl | 172–5 | 59.30, 6.16, | 6.59 ; | 59.11, 6.28, | 6.72 |
| 47 | —CH₂— | " | 2 | Ph | — | 124–5 | 70.98, 6.55, | 8.28 ; | 71.13, 6.52, | 8.43 |
| 48 | —CH₂— | " | 2 | 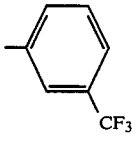 | 2HCl | 197–8 | 55.95, 5.40, | 6.53 ; | 55.73, 5.48, | 6.43 |
| 49 | —CH₂— | " | 2 | 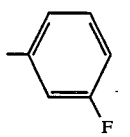 | " | 219–220 | 52.62, 4.84, | 5.84 ; | 52.74, 4.99, | 5.70 |
| 50 | —(CH₂)₂— | " | 2 | Ph | " | 196–8 | 59.30, 6.16, | 6.59 ; | 59.44, 6.23, | 6.45 |
| 51 | —(CH₂)₂— | " | 2 | 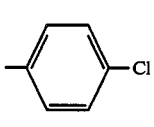 | " | 205–7 | 56.89, 5.68, | 6.32 ; | 57.17, 5.63, | 6.20 |
| 52 | —(CH₂)₂— | " | 2 | 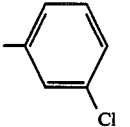 | — | 112–4 | 65.20, 5.99, | 7.24 ; | 65.03, 6.12, | 7.29 |
| 53 | —(CH₂)₂— | " | 2 | 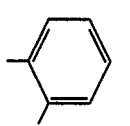 | 2HCl | 207–8 | 54.86, 5.48, | 6.09 ; | 54.99, 5.57, | 5.88 |
| 54 | —(CH₂)₂— | " | 2 | 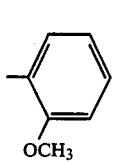 | " | 205–6 | 54.86, 5.48, | 6.09 ; | 55.03, 5.34, | 6.14 |
| 55 | —(CH₂)₂— | " | 2 |  | " | 215–7 | 58.03, 6.20, | 6.15 ; | 57.88, 6.05, | 6.27 |
| 56 | —(CH₂)₃— | " | 2 | Ph | " | 195–8 | 60.14, 6.42, | 6.38 ; | 60.43, 6.56, | 6.28 |

TABLE 3-continued

Structure:

$$\text{Z}\underset{O}{\overset{O}{\diagdown}}\text{-benzene-Y-(CH}_2)_n\text{-N(piperazine)N-R}$$

| No. | Z | Y | n | R | Addition salt | M.P. (°C.) | Elementary analysis C, H, N Calc. | ; | Found | |
|---|---|---|---|---|---|---|---|---|---|---|
| 57 | —CH₂— | " | 3 | Ph | " | 193–7 | 59.30, 6.16, 6.59 | ; | 59.17, 6.29, | 6.63 |
| 58 | —(CH₂)₂— | " | 3 | Ph | " | 205–8 | 60.14, 6.42, 6.38 | ; | 59.87, 6.35, | 6.34 |
| 59 | —(CH₂)₃— | " | 3 | Ph | " | 197–200 | 60.93, 6.67, 6.18 | ; | 61.19, 6.83, | 6.17 |
| 60 | —(CH₂)₃— | " | 3 | 4-F-C₆H₄ | " | 198–201 | 58.60, 6.20, 5.94 | ; | 58.51, 6.33, | 6.02 |
| 61 | —(CH₂)₃— | " | 3 | 3-CF₃-C₆H₄ | " | 187–191 | 55.29, 5.61, 5.37 | ; | 55.02, 5.65, | 5.49 |
| 62 | —(CH₂)₃— | " | 3 | 4-OCH₃-C₆H₄ | " | 201–4 | 59.63, 6.67, 5.79 | ; | 59.77, 6.59, | 5.91 |
| 63 | —(CH₂)₃— | " | 3 | 2-pyridyl | 3HCl | 191–4 | 53.83, 6.16, 8.56 | ; | 53.98, 6.03, | 8.34 |
| 64 | —CH₂— | " | 4 | Ph | 2HCl | 195–8 | 60.14, 6.42, 6.38 | ; | 59.83, 6.55, | 6.23 |
| 65 | —(CH₂)₂— | " | 4 | Ph | " | 204–6 | 60.93, 6.67, 6.18 | ; | 60.74, 6.64, | 6.27 |
| 66 | —(CH₂)₂— | " | 4 | 4-F-C₆H₄ | " | 191–3 | 58.60, 6.20, 5.94 | ; | 58.43, 6.33, | 5.79 |
| 67 | —(CH₂)₂— | " | 4 | 2-Cl-C₆H₄ | " | 205–8 | 56.63, 5.99, 5.74 | ; | 56.44, 6.08, | 5.49 |
| 68 | —(CH₂)₃— | " | 4 | Ph | " | 196–200 | 61.67, 6.90, 5.99 | ; | 61.59, 6.83, | 5.76 |
| 69 | —(CH₂)₃— | " | 4 | 2-OCH₃-C₆H₄ | " | 149–53 | 60.36, 6.89, 5.63 | ; | 60.30, 6.98, | 5.71 |
| 70 | —(CH₂)₂— | " | 5 | Ph | — | 102 | 73.06, 7.67, 7.10 | ; | 72.87, 7.60, | 7.13 |
| 71 | —CH₂— | " | 3 | 2-pyridyl | 3HCl | 137–140 | 51.91, 5.66, 9.08 | ; | 51.82, 5.76, | 10.01 |
| 72 | —(CH₂)₂— | " | 3 | 2-pyridyl | 3HCl | 170–2 | 52.90, 5.92, 8.81 | ; | 52.81, 5.84, | 8.99 |

TABLE 3-continued

![structure: benzodioxepine-Y-(CH2)n-N(piperazinyl)-N-R]

| No. | Z | Y | n | R | Addition salt | M.P. (°C.) | Elementary analysis C, H, N Calc. | ; | Found | |
|---|---|---|---|---|---|---|---|---|---|---|
| 73 | —CH$_2$— | " | 3 | (2-methoxyphenyl) | 2HCl | 192–4 | 58.03, 6.20, 6.15 | ; | 57.79; 6.31, | 6.06 |
| 74 | —(CH$_2$)$_2$— | " | 3 | " | " | 166–170 | 58.85, 6.44, 5.97 | ; | 58.69, 6.36, | 5.81 |
| 75 | —(CH$_2$)$_3$— | " | 3 | " | " | 195–6 | 59.63, 6.67, 5.79 | ; | 59.82, 6.53, | 5.81 |
| 76 | —(CH$_2$)$_2$— | " | 4 | " | " | 185–7 | 59.63, 6.67, 5.79 | ; | 59.39, 6.80, | 5.84 |
| 77 | —CH$_2$— | " | 4 | " | " | 185–7 | 58.85, 6.44, 5.97 | ; | 58.74, 6.54, | 6.02 |
| 78 | —(CH$_2$)$_3$— | " | 4 | (2-pyridyl) | 3HCl | 169–172 | 54.72, 6.39, 8.32 | ; | 54.79, 6.51, | 8.29 |
| 79 | —CH$_2$C(CH$_3$)$_2$CH$_2$— | " | 4 | (2-methoxyphenyl) | 2HCl | 144–7 | 61.71, 7.29, 5.33 | ; | 61.65, 7.40, | 5.21 |
| 80 | —CH$_2$— | —NHCH$_2$— | 2 | Ph | 3HCl | 113–5 | 53.52, 6.29, 9.36 | ; | 53.23, 6.39, | 9.22 |
| 81 | —CH$_2$— | —N(COCH$_3$)CH$_2$— | 1 | (2-methoxyphenyl) | 2HCl | 154–6 | 56.17, 6.21, 8.93 | ; | 56.31, 6.15, | 9.10 |
| 82 | —(CH$_2$)$_3$— | —NHCH$_2$— | 2 | " | 3HCl | 154–8 | 55.34, 6.97, 8.07 | ; | 55.19, 6.88, | 8.19 |

*Ph: phenyl

The following compounds can be prepared in the same manner as disclosed in the above examples:
7-[7-(4-phenyl-1-piperazinyl)heptanoyl]-1,5-benzodioxepine
7-[5-[4-(2-methoxyphenyl)-1-piperazinyl]valeryl]-3-ethyl-3-propyl-1,5-benzodioxepine
7-[4-[4-(2-pyridyl)-1-piperazinyl]-1-hydroxybutyl]-3-ethyl-1,5-benzodioxepine
N-[3-(4-phenyl-1-piperazinyl)propyl]-N-ethyl-3,4-methylenedioxyaniline
7-[5-[4-(2-ethylphenyl)-1-piperazinyl]valeryl]-1,5-benzodioxepine
6-[5-[4-(4-butylphenyl)-1-piperazinyl]valeryl]-1,4-benzodioxane
7-[5-[4-(2-ethoxyphenyl)-1-piperazinyl]valeryl]-1,5-benzodioxepine
7-[5-[4-(2-butoxyphenyl)-1-piperazinyl]valeryl]-1,5-benzodioxepine
7-[4-[4-(3,4-dichlorophenyl)-1-piperzinyl]butyryl]-1,5-benzodioxepine
7-[4-[4-(3-methyl-4-methoxyphenyl)-1-piperazinyl]butyryl]-1,5-benzodioxepine
6-[4-[4-(4-bromophenyl)-1-piperazinyl]-1-hydroxybutyl]-1,5-benzodioxane

Having now fully described the invention, it will be apparent to one of ordinary skill in the art that many changes and modifications can be made thereto without departing from the spirit or scope of the invention as set forth herein.

What is claimed as new and intended to be covered Letters Patent is:

1. A method of treating a hypertensive subject, comprising:
   administering to said hypertensive subject a therapeutically effective amount of an alkylenedioxybenzene compound of the formula:

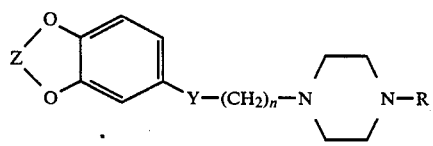

wherein n is an integer of 1 to 6; Z is —(CH$_2$)$_m$—, wherein m is an integer of 1 to 3 or

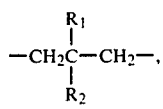

wherein $R_1$ is hydrogen or $C_1$-$C_3$ alkyl and $R_2$ is $C_1$-$C_3$ alkyl; Y is —CH(OH)—,

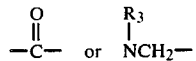

wherein $R_3$ is hydrogen, $C_1$-$C_3$ alkyl or $C_1$-$C_3$ acyl; and R is phenyl, phenyl substituted by at least one substituent selected from the group consisting of halogen, $C_1$-$C_5$ alkyl, $C_1$-$C_5$ alkoxy and trifluoromethyl, or pyridyl, or an acid addition salt thereof, the extent of substitution of said phenyl ring being such that said alkylenedioxybenzene compound must possess significant hypotensive activity.

2. The method of claim 1, wherein n is an integer of 1 to 5; Z is —$(CH_2)_m$—, wherein m is an integer of 1 to 3 or

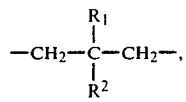

wherein $R_1$ and $R_2$ are $C_1$-$C_3$ alkyl; and Y is —CH(OH)—,

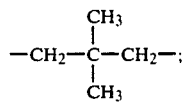

wherein $R_3$ is hydrogen or $C_1$-$C_3$ acyl.

3. The method of claim 2, wherein n is an integer of 1 to 4; Z is —$(CH_2)_m$—, wherein m is an integer of 1 to 3 or $$-CH_2-\underset{\underset{CH_3}{|}}{\overset{\overset{CH_3}{|}}{C}}-CH_2-;$$

Y is —CH(OH)—,

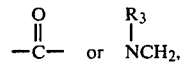

wherein $R_3$ is acetyl; and R is phenyl, pyridyl, or phenyl substituted by chloro or methoxy, or an acid addition salt thereof.

* * * * *